US005665084A

United States Patent [19]
Richmond

[11] Patent Number: 5,665,084
[45] Date of Patent: Sep. 9, 1997

[54] ATTACHABLY PRESSURE SENSITIVE APPARATUS FOR INCREASING GIRTH OF DISPOSABLE UNDERGARMENTS AND INCONTINENT DEVICES

[76] Inventor: Luke T. Richmond, The Wind Works, 3333 S. Center Rd., Burton, Mich. 48519

[21] Appl. No.: 639,171

[22] Filed: Apr. 26, 1996

[51] Int. Cl.$^6$ .............................. A61F 13/15; A61F 13/20
[52] U.S. Cl. ..................... 604/389; 604/390; 604/385.1
[58] Field of Search .......................... 604/385.1, 389, 604/390, 391, 394

[56] References Cited

U.S. PATENT DOCUMENTS

| | | | |
|---|---|---|---|
| 4,578,072 | 3/1986 | Lancaster | 604/389 |
| 4,670,012 | 6/1987 | Johnson | 604/389 |
| 5,092,862 | 3/1992 | Muckenfuhs et al. | 604/389 |

FOREIGN PATENT DOCUMENTS

92/01759  2/1992  WIPO.

Primary Examiner—Robert A. Clarke
Assistant Examiner—Ki Yong O

[57] ABSTRACT

A device for use in association with a diaper is provided. The diaper has a central extent positionable between legs of a child. A horizontal forward edge and a horizontal rearward upper edge are positionable in front of and behind the child. Upper front sides and upper rear sides are joined on each side of the child. An adhesive tab is secured to each upper front side of the diaper. A pair of diaper extenders are provided. One diaper extender is positioned over one upper rear side of the diaper. Each of the extenders includes a generally inextensible planar sheet which has parallel upper and lower edges with a longitudinal axis centrally therebetween and parallel front and rear edges therebetween. A planar adhesive strip has long upper and lower horizontal parallel edges with a longitudinal axis centrally therebetween. The adhesive strip has adhesive on one surface thereof. About half of the length of the adhesive strip is adhesively secured to the sheet and about half of the length of the adhesive strip is adhesively secured to the diaper at the respective upper rear edge thereby eliminating contact of a sharp edge of the adhesive sheet with a wearer's skin. A logo on the surface of the adhesive strip opposite from the surface of the adhesive. The logo is adjacent to the end of the adhesive strip remote from the inextensible sheet.

4 Claims, 3 Drawing Sheets

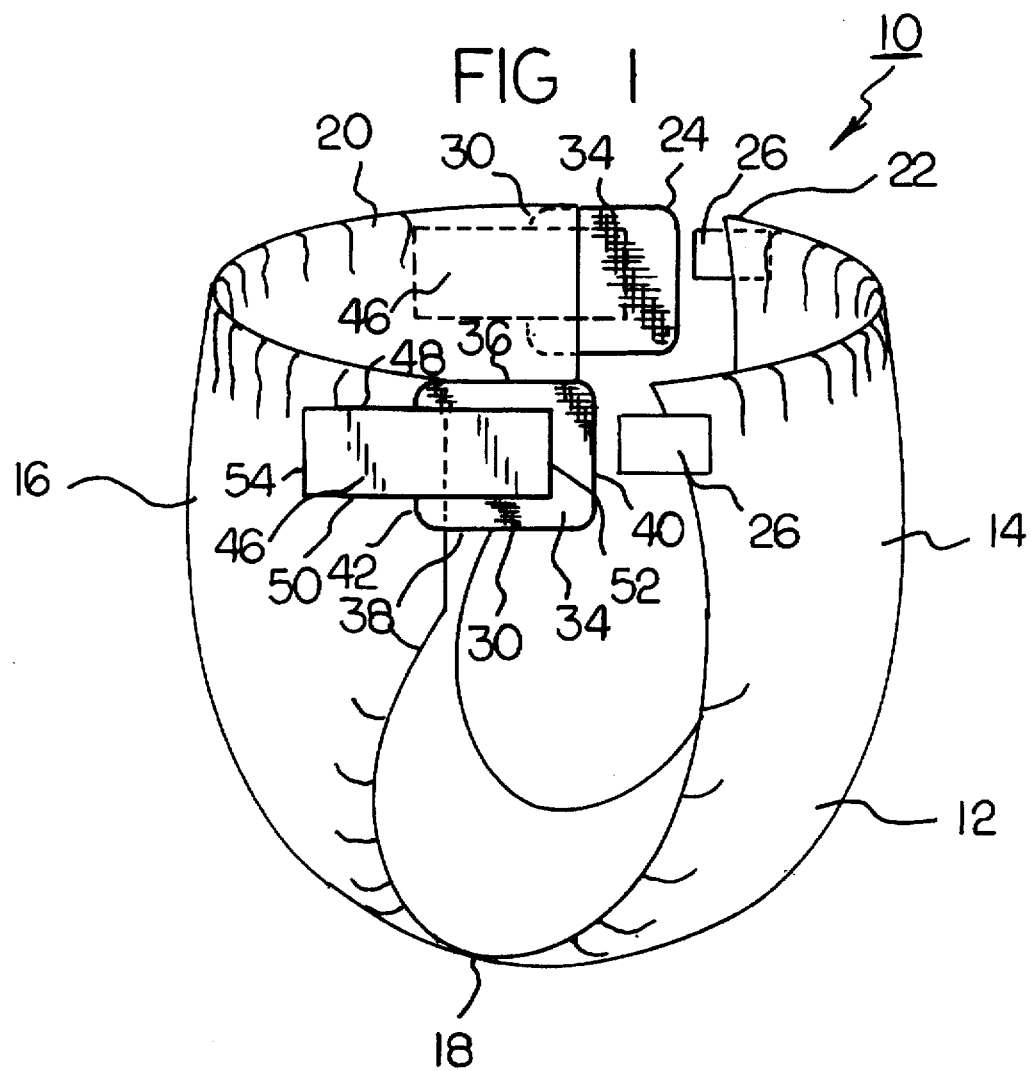
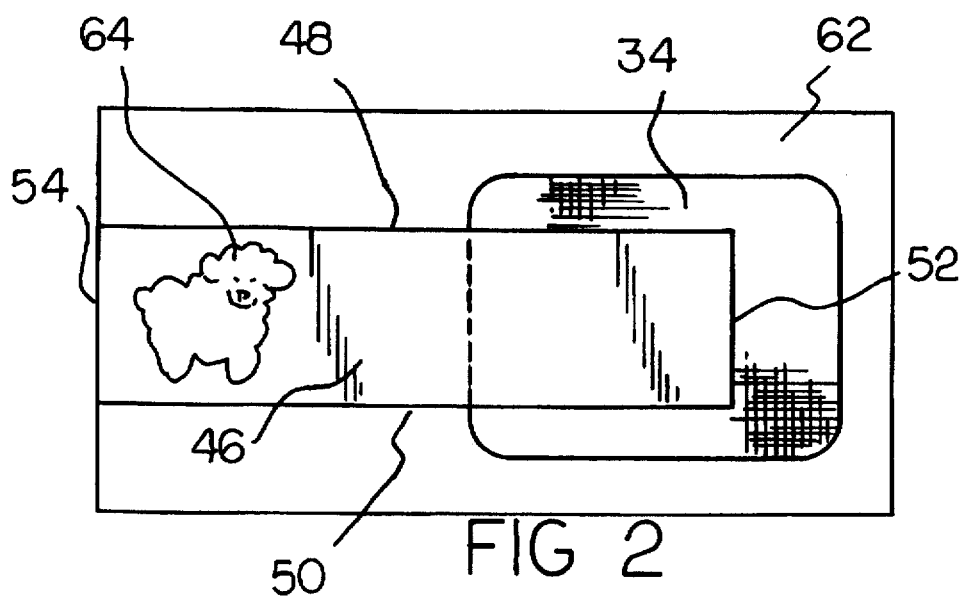

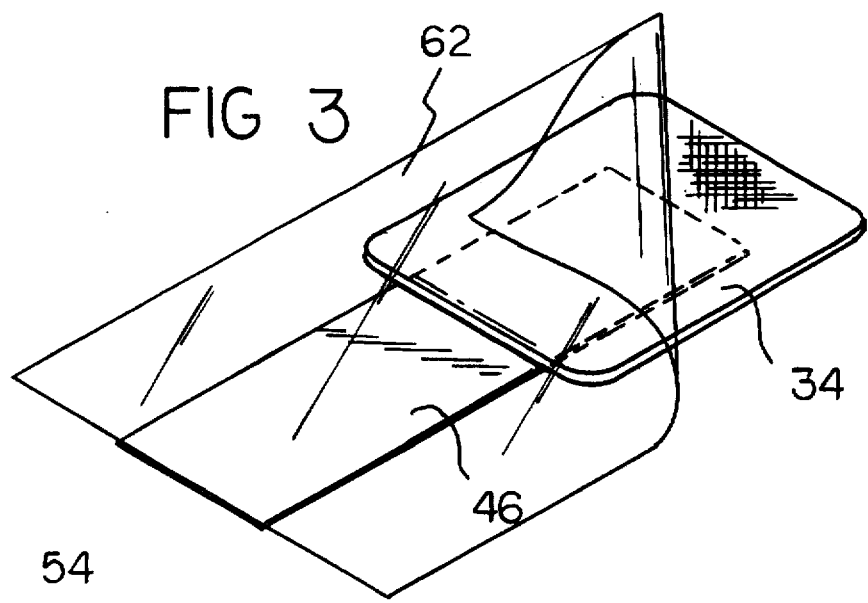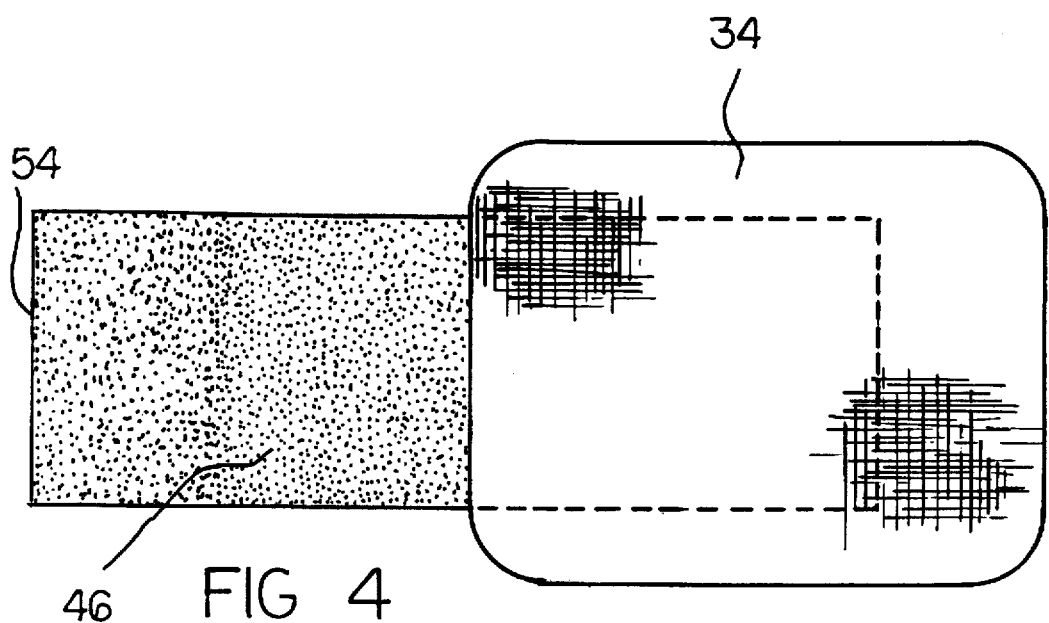

FIG 5
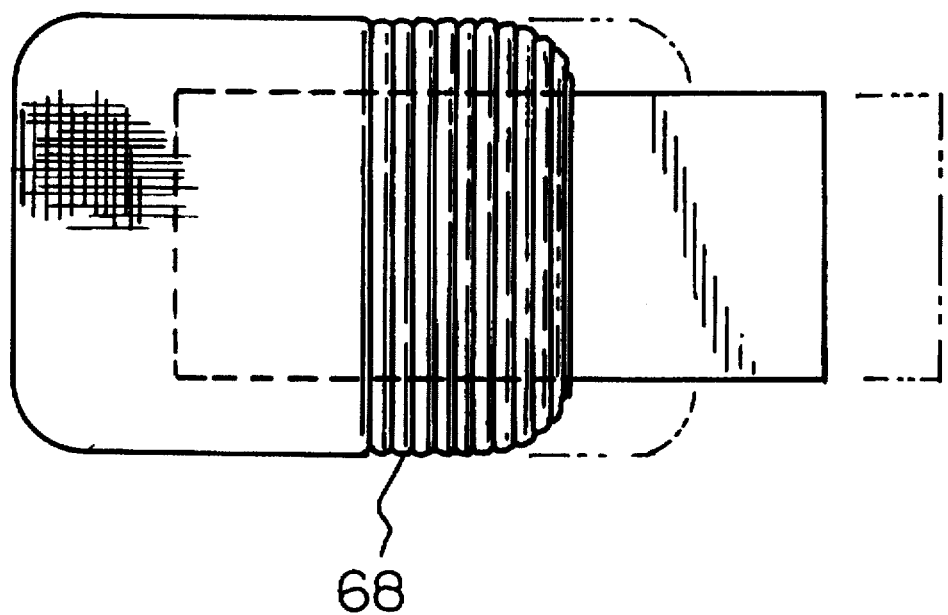
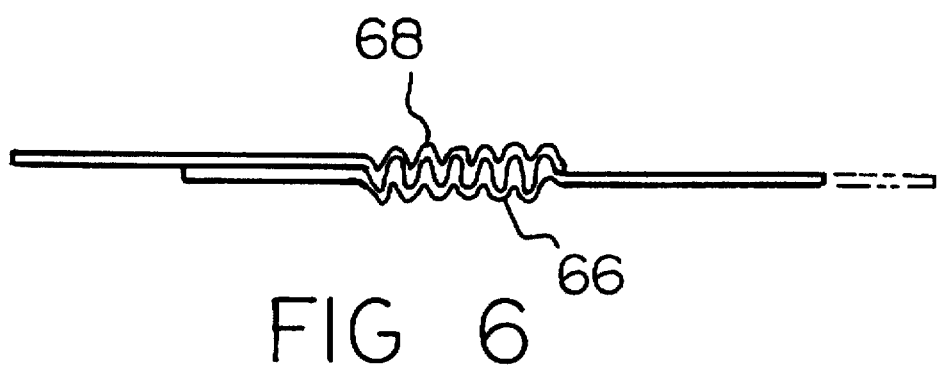
FIG 6

ATTACHABLY PRESSURE SENSITIVE APPARATUS FOR INCREASING GIRTH OF DISPOSABLE UNDERGARMENTS AND INCONTINENT DEVICES

BACKGROUND OF THE INVENTION

1. Field of the Invention

The present invention relates to new and improved attachably pressure sensitive apparatus for increasing girth of disposable undergarments and incontinent devices and, more particularly, pertains to allowing standard sized diapers to be used on nonstandard sized persons through the use of side extenders.

2. Description of the Prior Art

The use of tabs for the sides of diapers is known in the prior art. More specifically, tabs for the sides of diapers heretofore devised and utilized for the purpose of attaching diapers through securement means at their sides are known to consist basically of familiar, expected, and obvious structural configurations, notwithstanding the myriad of designs encompassed by the crowded prior art which has been developed for the fulfillment of countless objectives and requirements.

The prior art discloses a large number of tabs for the sides of diapers. By way of example, U.S. Pat. No. 3,897,293 to Babcock discloses a method for applying adhesive tape tabs to a disposable diaper.

U.S. Pat. No. 4,063,559 to Tritsch discloses a disposable diaper having stretchable adhesive tab fasteners with partible protective film.

U.S. Pat. Nos. 5,028,646 and 5,112,889 to Miller discloses pressure-sensitive adhesive composition, tape and diaper closure systems.

U.S. Pat. No. 5,071,415 to Takemoto discloses novel adhesive means for releasably fastening disposable diapers or other articles of clothing.

Lastly, U.S. Pat. No. 5,108,384 to Goulait discloses a disposable absorbent article with combination mechanical and adhesive tape fastener system and having reserve adhesive tape for improved disposability.

In this respect, the attachably pressure sensitive apparatus for increasing girth of disposable undergarments and incontinent devices according to the present invention substantially departs from the conventional concepts and designs of the prior art, and in doing so provide an apparatus primarily developed for the purpose of allowing standard sized diapers to be used on nonstandard sized persons through the use of side extenders.

Therefore, it can be appreciated that there exists a continuing need for new and improved devices for attachment to diapers to allow standard sized diapers to be used on nonstandard sized persons through the use of side extenders. In this regard, the present invention substantially fulfills this need.

SUMMARY OF THE INVENTION

In view of the foregoing disadvantages inherent in the known types of tabs for the sides of diapers now present in the prior art, the present invention provides the only attachably pressure sensitive apparatus for increasing girth of disposable undergarments and incontinent devices. As such, the general purpose of the present invention, which will be described subsequently in greater detail, is to provide new and improved attachably pressure sensitive apparatus for increasing girth of disposable undergarments and incontinent devices and methods which have all the advantages of the prior art and none of the disadvantages.

To attain this, the present invention essentially comprises a new and improved attachment system in combination with a diaper to allow diaper usage for larger children comprising a diaper. The diaper has a central extent positionable between the legs of a child, with a horizontal forward edge and a horizontal rearward upper edge positionable in the front and rear of a child and defining an upper front side and an upper rear side to be joined on each side of the child during wearing. A pair of diaper extenders, are provided. One extender is positioned over each upper rear side of a diaper. Each of the extenders includes a generally inextensible sheet formed in a rectangular configuration and has parallel upper and lower edges about 3⅛ inches in length with a longitudinal axis centrally therebetween and parallel front and rear edges about 2¾ inches in height therebetween. Each sheet has a minority of its extent located over an upper rear side of the diaper. Each of the extenders also includes an adhesive strip. The adhesive strip has long upper and lower horizontal parallel edges about 5½ inches in length with a longitudinal axis centrally therebetween and short vertical end edges about 1⅞ inches in height therebetween. Each adhesive strip has adhesive on one surface thereof. About half of the length of the adhesive strip is adhesively secured to the sheet and about half of the length of the adhesive strip is adhesively secured to the diaper at the upper rear edge with their axes overlapping. The adhesive strip overlaps between about 50 percent and 65 percent of the area of the inextensible sheet. A piece of covering material of a height of about 6½ inches and of a length of about 2⅝ inches is provided to cover that portion of the adhesive strip remote from the inextensible sheet and a portion of its length over the inextensible sheet. The rear edge of the adhesive strip and the adjacent edge of the covering material are essentially coextensive whereby, when the covering material is removed, it will expose the adhesive for securement to the upper rear side of the diaper while allowing the opposite edge of the sheet free for contact and securement with an adhesive tab of the diaper. An adhesive tab is secured to each upper front side of the diaper at its forward edge and to the forward edge of the sheet.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved attachably pressure sensitive apparatus for increasing girth of disposable undergarments and incontinent devices which has all the advantages of the prior art tabs for the sides of diapers and none of the disadvantages.

It is another object of the present invention to provide new and improved attachably pressure sensitive apparatus for increasing girth of disposable undergarments and incontinent devices which may be easily and efficiently manufactured and marketed.

It is a further object of the present invention to provide new and improved attachably pressure sensitive apparatus for increasing girth of disposable undergarments and incontinent devices which are of a durable and reliable construction.

An even further object of the present invention is to provide new and improved attachably pressure sensitive apparatus for increasing girth of disposable undergarments and incontinent devices which are susceptible of a low cost of manufacture with regard to both materials and labor, and which accordingly are then susceptible of low prices of sale to the consuming public, thereby making such tabs for the sides of diapers economically available to the buying public.

Still yet another object of the present invention is to provide new and improved attachably pressure sensitive apparatus for increasing girth of disposable undergarments and incontinent devices which provide in the apparatuses and methods of the prior art some of the advantages thereof, while simultaneously overcoming some of the disadvantages normally associated therewith.

Even still another object of the present invention is to allow smaller diapers to be used on larger children through the use of side extenders.

Lastly, it is an object of the present invention to provide a device for use in association with a diaper. The device has a central extent positionable between legs of a child, a horizontal forward edge and a horizontal rearward upper edge positionable in front of and behind the child, respectively. Upper front sides and upper rear sides to be joined on each side of the child during wearing. An adhesive tab is secured to each upper front side of the diaper at a forward edge thereof. The device further includes a pair of diaper extenders for securement to a respective adhesive tab to allow diaper usage for larger children. One diaper extender is positioned over one upper rear side of the diaper respectively. Each of the extenders includes a generally inextensible planar sheet formed in a rectangular configuration which has parallel upper and lower edges with a longitudinal axis centrally therebetween and parallel front and rear edges therebetween. A planar adhesive strip has long upper and lower horizontal parallel edges with a longitudinal axis centrally therebetween. The parallel edges are longer than the length of the upper and lower edges of the sheet and have short vertical end edges therebetween. The adhesive strip has adhesive on one surface thereof. About half of the length of the adhesive strip is adhesively secured to the sheet and about half of the length of the adhesive strip is adhesively secured to the diaper at the respective upper rear edge. A logo on the surface of the adhesive strip opposite from the surface of the adhesive. The logo is adjacent to the end of the adhesive strip remote from the inextensible sheet.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the preferred embodiment of the new and improved attachably pressure sensitive apparatus for increasing girth of disposable undergarments and incontinent devices constructed in accordance with the principles of the present invention.

FIG. 2 is a front elevational view of one of the extender devices shown in FIG. 1.

FIG. 3 is a perspective view of the device of FIG. 2 with the peel-off strip partially removed.

FIG. 4 is an enlarged front elevational view similar to FIG. 2 but with the peel-off sheet fully removed.

FIG. 5 is an enlarged front elevational view of another embodiment.

FIG. 6 is a cross-sectional view of FIG. 5 taken at a point corresponding to section line 6—6.

The same reference numerals refer to the same parts throughout the various Figures.

DESCRIPTION OF THE PREFERRED EMBODIMENT

With reference now to the drawings, and in particular to FIG. 1 thereof, the preferred embodiment of the new and improved attachably pressure sensitive apparatus for increasing girth of disposable undergarments and incontinent devices embodying the principles and concepts of the present invention and generally designated by the reference numeral 10 will be described. As used herein, the term larger children is intended to include children of larger size as well as incontinent devices.

The present invention, the new and improved attachably pressure sensitive apparatus for increasing girth of disposable undergarments and incontinent devices, is comprised of a plurality of components. Such components include the diaper extenders, inextensible sheets, adhesive strips, and covering material. Each of the individual components is specifically configured and correlated one with respect to the other so as to attain the desired objectives.

More specifically, the present invention is a system 10 and is adapted to be used upon a diaper 12. The diaper is of a conventional construction with a panel formed to create a front section 14 and a rear section 16. It is closed at the bottom 18 and opened at the top 20. The front upper edge 22 and the rear upper edge 24 are adapted to be coupled through adhesive tabs 26 permanently secured at the upper front edge and adhesively secured during diapering to the upper rear edge.

The present invention has for its major component a pair of diaper extenders 30. One diaper extender is adapted to be positioned on each upper rear side of the diaper with its forward end adapted to be coupled to the adhesive tab, one secured to each upper front side of the diaper. FIG. 1 is an illustration of the extender tabs secured to a diaper in anticipation for final coupling with the tab for operation and use on a child.

Each of the extenders includes a generally inextensible sheet 34. The sheet is of a cottony flannel-like fabric, preferably soft feeling, for the comfort of a child. Each sheet is formed in a rectangular configuration and has parallel upper and lower edges 36 and 38. A longitudinal axis extends centrally therebetween. Parallel front and rear edges 40 and 42 extend between the upper and lower edges.

Each of the extenders also includes an adhesive strip 46. Each such adhesive strip has long upper and lower parallel edges 48 and 50. A longitudinal axis is located centrally therebetween. The upper and lower edges are of a length longer than the upper edges of the sheet. The adhesive strips each have short end edges 52 and 54 between the upper and lower edges. The length of the short edges is shorter than the front and rear edges of the sheet.

The adhesive strips each have an adhesive 58 on one surface thereof, the interior surface. A commercially available contact adhesive could readily be utilized. It is preferred, however, to utilize an adhesive which is ecologically safe in the event of inadvertent contact with the child wearing the diaper. The majority of the length of the adhesive strip is adhesively secured to the sheet when purchased. Such adhesive is secured to the sheet to couple the strip and sheet with their axes being overlapped.

The next component of the extender is a piece of covering material 62. The material is in a rectangular configuration. It has a height substantially equal to the height of the adhesive strip. It is of a length to cover that portion of the adhesive strip remote from the sheet and to allow a portion of its length to extend over the sheet and not in adhesive contact therewith. In this manner, a user may grasp that portion of the covering over the sheet to remove it and expose the adhesive for securement to the upper rear side of the diaper. This allows the remaining portion of the sheet to extend forwardly for contact and securement with the adhesive tab of the diaper.

In this manner, a diaper may be placed on the child with the upper front side and upper rear side of the diaper out of contact but operatively coupled through the extender.

The inextensible sheet 34 has a length in the preferred embodiment of about 3⅛ inches and a height of about 2¾ inches. This is about 8.6 square inches. The adhesive strip 46 has a length of about 5½ inches and a height of about 1⅞ inches. It has an area of about 10.3 square inches. The covering material 62, a throw-away piece, has a length of about 6½ inches and a height of about 3⅞ inches. Its total area is about 25.2 square inches. The area of overlap between the adhesive strip and the inextensible sheet is about 2⅝ inches along the lengths of such two pieces of the system. In this manner, between about 50 percent and 65 percent of the inextensible sheet is covered and secured by the adhesive strip, preferably about 57 percent. About half of the length of the adhesive strip is coupled directly to the inextensible sheet while about half of the length of the adhesive strip is coupled directly to the covering material. This allows for maximum strength of retention of the components of the system, the inextensible sheet, the adhesive strip and the covering material. Further, it is noted that the edge 54 of the adhesive strip remote from the inextensible sheet is essentially coextensive with the adjacent edge of the covering material 62. Such coextensive edges also simplify the fabrication process of the extenders of the present invention. This arrangement results in an arrangement where a user is naturally inclined to separate the covering material from the inextensible sheet and adhesive strip by grasping the inextensible sheet and adhesive strip in a region where the adhesive strip is not coupled directly to the covering material.

In this regard, an indicia 64 is placed on the exterior surface of the adhesive strip at a region remote from the inextensible sheet. In this manner, such indicia can be seen only from the side of the adhesive strip remote from the inextensible sheet. This assists the user in removing the inextensible sheet and adhesive strip from the covering material in anticipation of usage. It also ensures that the inextensible sheet and adhesive strip are properly positioned with the adhesive located interiorly in contact with the diaper since the indicia is visible only when the adhesive strip and inextensible sheet are properly positioned with respect to the diaper upon it is utilized.

Desperate parents can diaper their larger babies and older babies that need diapers at bedtime. Youngsters that may be potty trained, but are ill, could now use diapers for protection. Although the largest diaper available can be forced on children over 36 pounds, the tape tends to cut, irritate and blister the child's tender skin. The present invention protects children's skin.

Retailers that must now stock all of the numerous brands and sizes of diapers will now feel that they are covering all the bases (sizes) by simply stocking a few diapers plus the present invention, thus saving huge overhead costs.

Often children will need to move up in available diaper sizes to achieve a good waist size, but otherwise the diaper is too big. Thus, although it fits in circumference it tends to hang below the knees. The present invention enables the child to stay in the smaller size longer in order to keep the good fit in the crotch. Children between sizes can get a perfect fit with the present invention which precludes a pinched waist or a sagging diaper. Further, large and older children that are ill or need to continue using diapers at night for protection will be able to use disposables.

The present invention serves to remedy a number of problems. Adults or babies that tend to play with, and scratch under pile type fasteners or button elastic fasteners will be less likely to play with or touch their diaper because of the smoother fit and feel of their disposable diaper with a diapers adapter attached. Since babies skin is sensitive and elderly skin is thinner, adhesive tabs touching the skin from a diaper that is too small can do painful damage to the wearer. The present invention will remedy this problem. After a diaper has been worn for a period of time, many diaper wearers experience a roping effect. In this situation, the front panel tends to wrap itself and is drawn to the tape area making a rope-like structure which can be uncomfortable or painful for the user. The present invention strengthens this area and prevents this rope effect from occurring. Many babies have extremely large thighs and need extra room in the leg area. The present invention provides this extra room. Many adults have the same problems as children do, big thighs, big sides, the roping effect. No matter how many standard sizes of diapers there are, only the present invention can meet the need caused by the endless variety of sizes of adults. If the diaper is not big enough, it can be made bigger. If someone has something beside the average size or shape, they will be using the present invention. Diapers which are too tight, just like underwear which is too tight, tends to cause gas in the wearer. The present invention solves this problem.

The present invention provides a device that extends an adhesive strip over nearly the entire length of the sheet whereas most similar prior art devices merely attach the adhesive strip to the sheet at its edge. Superior strength is achieved by not having the load of the undergarment spread over an additional seam or weak spot which would otherwise be between the sheet and adhesive strip. Instead a single consistent strip bears the weight of the diaper. The adhesive strip material is receptive by its nature to receive the fixing strip of the diaper. Additionally, rather than cutting the sheet in line with the same edge as the adhesive strip the sheet must extend somewhat beyond this edge, this critical feature allows us to use these components in an unexpected manner. This sheet not only protects the wearer from becoming taped themselves, but also protects from the irritating edge of the adhesive strip.

Also, even when disposables seem to fit, the strong tape of the diaper can work its way through to the child's skin. The present invention can help protect from this type of scratching and blistering. The present invention may also be utilized in a similar manner on adult incontinence devices.

As to the manner of usage and operation of the present invention, the same should be apparent from the above description. Accordingly, no further discussion relating to the manner of usage and operation will be provided.

What is claimed as being new and desired to be protected by LETTERS PATENT of the United States is as follows:

1. An attachment system in combination with a diaper to allow diaper usage for larger children comprising:

a diaper having a central extent positionable between the legs of a child, with a horizontal forward edge and a horizontal rearward upper edge positionable in the front and rear of a child and defining a pair of upper front sides and a pair of upper rear sides to be joined on each side of the child during wearing;

a pair of diaper extenders, one positioned over each upper rear side of a diaper, each of the extenders including an inextensible sheet formed in a rectangular configuration having parallel upper and lower horizontal edges forming a length of about 3⅛ inches with a longitudinal axis centrally therebetween and parallel front and rear vertical edges forming a height of about 2¾ inches therebetween, each sheet having a minority of its extent located over an upper rear side of the diaper;

each of the extenders also including an adhesive strip having long upper and lower horizontal parallel edges forming a length of about 5½ inches with a longitudinal axis centrally therebetween and having short vertical end edges forming a height of about 1⅞ inches therebetween, each adhesive strip having adhesive fully covering one surface thereof, about half of the length of the adhesive strip being adhesively secured to the sheet and about half of the length of the adhesive strip being adhesively secured to the diaper at the upper rear edge with their axes being overlapped, the adhesive strip overlapping between about 50 percent and 65 percent of the area of the inextensible sheet;

a piece of covering material having a length of about 6½ inches and of a height of about 2⅝ inches to cover that portion of the adhesive strip remote from the inextensible sheet prior to coupling to a diaper and a portion of its length over the inextensible sheet, the rear edge of the adhesive strip and the adjacent edge of the covering material being essentially coextensive whereby, when the covering material is removed, it will expose the adhesive for securement to the upper rear side of the diaper while allowing the opposite edge of the sheet free for contact and securement with an adhesive tab of the diaper; and an adhesive tab secured to each upper front side of the diaper at its forward edge and secured to the forward edge of the sheet.

2. For use in association with a diaper of the type having a central extent positionable between legs of a child, a horizontal forward edge and a horizontal rearward upper edge positionable in front of and behind the child, respectively, a pair of upper front sides and upper rear sides to be joined on each side of the child during wearing, and an adhesive tab secured to each upper front side of the diaper at a forward edge thereof;

a pair of diaper extenders for securement to a respective adhesive tab to allow diaper usage for larger children, one diaper extender positioned over each upper rear side of the diaper respectively;

each of the extenders including:

an inextensible planar sheet formed in a rectangular configuration having parallel upper and lower horizontal edges forming a length with a longitudinal axis centrally therebetween and parallel vertical front and rear edges therebetween;

a planar adhesive strip having long upper and lower horizontal parallel edges with a longitudinal axis centrally therebetween, said upper and lower parallel edges of the strip being of a length longer than the length of the upper and lower edges of the sheet and having vertical end edges therebetween forming a height less than the height of the end edges of the sheet, said adhesive strip having adhesive fully covering one surface thereof, about half of the length of the adhesive strip being adhesively secured to the sheet and about half of the length of the adhesive strip being adhesively securable to the diaper at the respective upper rear edge;

a covering material adhered to each adhesive strip prior to being coupled to a diaper, the covering material having a length greater than the length of the upper and lower edges of the sheet with the height of the covering material being greater than the height of the end edges of the coupled sheet and adhesive strip.

3. The extenders as set forth in claim 2 wherein the rear edge of the adhesive strip and the adjacent edge of the covering material are essentially coextensive.

4. The extenders as set forth in claim 2 and further including a logo on the surface of the adhesive strip opposite from the surface having the adhesive, the logo being adjacent to the end of the adhesive strip remote from the inextensible sheet.

* * * * *